United States Patent [19]

Jordan et al.

[11] Patent Number: Plant 6,680

[45] Date of Patent: Mar. 21, 1989

[54] CHRYSANTHEMUM PLANT NAMED GEOS

[75] Inventors: Christine Jordan, Tenerife, Spain; Marie Satory, Hamburg, Fed. Rep. of Germany

[73] Assignee: Ball Seed Company, West Chicago, Ill.

[21] Appl. No.: 114,402

[22] Filed: Oct. 28, 1987

[51] Int. Cl.[4] ..... A01H 5/00

[52] U.S. Cl. ..... Plt./77

[58] Field of Search ..... Plt./74–82

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Geos having large, fully double, creamy white ray florets, compact growth habit, nine week flowering response, and excellent performance under low light conditions.

1 Drawing Sheet

The present invention comprises a new and distinct cultivar of *Chrysanthemum morifolium,* hereinafter referred to by the cultivar name Geos.

Geos is a product of a planned breeding program which had the objective of creating new Chrysanthemum cultivars with large white decorative flowers, excellent growth habit and pot plant performance under low light winter conditions. Such traits in combination were not present or needed improvement in previously available commercial cultivars.

Geos was originated from a hybridization made by applicants in a controlled breeding program in Ahrensburg, Federal Republic of Germany in 1978. The male and female parents were unnamed seedlings. Geos was discovered and selected as one flowering plant within the progeny of the stated parentage by applicants in 1978 in a controlled environment in Ahrensburg, Federal Republic of Germany.

The first act of asexual reproduction of Geos was accomplished when vegetative cuttings were taken from the initial selection in 1979 in a controlled environment in Ahrensburg, Federal Republic of Germany by a technician working under formulations established and supervised by applicants. Horticultural examination of selected units initiated in 1979 has demonstrated that the combination of characteristics as herein disclosed for Geos are firmly fixed and are retained through successive generations of asexual reproduction.

The following traits have been repeatedly observed and are determined to be basic characteristics of Geos, which in combination distinguish this Chrysanthemum as a new and distinct cultivar:

1. Nine week response period.
2. Compact growth habit.
3. Creamy white flower color.
4. Fully double flower with no disc florets present.
5. Diameter of capitulum 8–13 cm.
6. Florets range up to 55 mm at outer edge of capitulum (fully expanded petals).
7. Superior keeping and shipping quality.
8. Finished height 25–30 cm from top edge of the pot depending upon growing conditions.
9. Excellent low light performance.

Geos has not been observed under all possible environmental conditions. The phenotype may vary significantly with variations in environment such as temperature, light intensity, and day length.

The following observations, measurements and comparisons describe plants grown in Parrish, Fla. under greenhouse conditions which approximate those generally used in commercial practice.

Of the many commercial cultivars known to the present inventors, the most similar in comparison to Geos is Mt. Snow. In comparison to Mt. Snow, Geos has a creamier flower color, more compact habit, and is one (1) week earlier in flowering.

The accompanying photographic drawing shows typical inflorescense and foliage characteristics of Geos, with colors being as nearly true as possible with illustrations of this type. The photograph is in black and white, with two flowers being colored to accurately depict the immature and mature ray floret colors.

In the following description color references are made to the Royal Horticultural Society Colour Chart. The color values were determined between 3:45 and 4:00 p.m. on Sept. 9, 1987 under fluorescent lighting at Parrish, Fla.

Classification:

*Botanical.*—*Chrysanthemum morifolium,* cv. Geos.

Commercial.—Decorative pot.

INFLORESCENCE

A. Capitulum:

*Form.*—Flat.

*Type.*—Double.

*Diameter across face.*—8–13 cm.

B. Corolla of ray florets

*Color (general tonality from a distance of three meters).*—White.

*Color (upper surface).*—Immature ray florets 8C; mature, fully expanded ray florets 155B.

*Color (under surface).*—Immature ray florets 8D; mature, fully expanded ray florets 155B.

C. Corolla of disc florets: None present.

D. Reproductive organs:

*Androecium.*—Absent.

*Gynoecium.*—Present in ray florets.

PLANT

A. General appearance:

*Height.*—Finished height 25–30 cm from top edge of the pot depending upon growing conditions.

B. Foliage:

*Color (upper surface).*—147A.

*Color (under surface).*—147B.

*Shape.*—Ovate, deeply lobed and slightly serrate margins.

We claim:

1. A new and distinct cultivar of Chrysanthemum plant named Geos, as illustrated and described, and parts thereof.

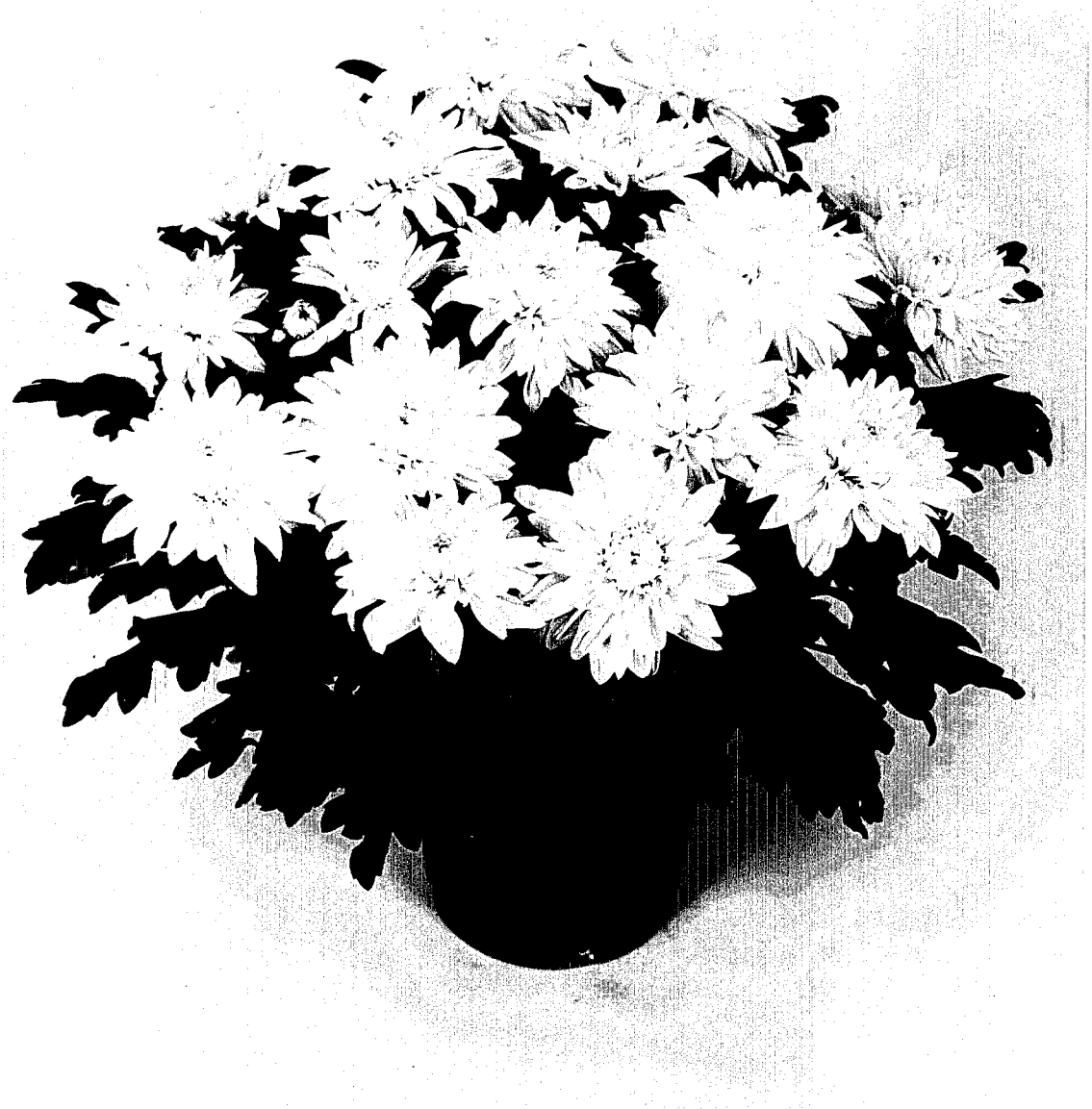

* * * * *